(12) United States Patent
Johnson et al.

(10) Patent No.: US 8,934,992 B2
(45) Date of Patent: Jan. 13, 2015

(54) NERVE CUFF

(75) Inventors: Blake D. Johnson, Plymouth, MN (US); Mark Christopherson, Shoreview, MN (US); John Rondoni, Plymouth, MN (US); Quan Ni, Shoreview, MN (US)

(73) Assignee: Inspire Medical Systems, Inc., Maple Grove, MN (US)

( * ) Notice: Subject to any disclaimer, the term of this patent is extended or adjusted under 35 U.S.C. 154(b) by 0 days.

(21) Appl. No.: 13/600,572

(22) Filed: Aug. 31, 2012

(65) Prior Publication Data

US 2013/0231726 A1 Sep. 5, 2013

Related U.S. Application Data

(60) Provisional application No. 61/530,002, filed on Sep. 1, 2011.

(51) Int. Cl.
*A61N 1/05* (2006.01)

(52) U.S. Cl.
CPC ..................................... *A61N 1/0556* (2013.01)
USPC ......................................................... 607/118

(58) Field of Classification Search
None
See application file for complete search history.

(56) References Cited

U.S. PATENT DOCUMENTS

| | | |
|---|---|---|
| 3,654,933 A | 4/1972 | Hagfors |
| 4,379,462 A | 4/1983 | Borkan |
| 4,512,351 A | 4/1985 | Pohndorf |
| 4,567,892 A | 2/1986 | Plicchi |
| 4,590,946 A * | 5/1986 | Loeb .............................. 600/375 |
| 4,602,624 A | 7/1986 | Naples et al. |
| 4,628,614 A | 12/1986 | Thompson |
| 4,960,133 A | 10/1990 | Hewson |
| 4,967,755 A | 11/1990 | Pohndorf |
| 5,158,080 A | 10/1992 | Kallok |
| 5,178,156 A | 1/1993 | Takishima |
| 5,265,624 A | 11/1993 | Bpwman |
| 5,282,468 A | 2/1994 | Klepinski |
| 5,324,322 A | 6/1994 | Grill, Jr. et al. |

(Continued)

FOREIGN PATENT DOCUMENTS

| | | |
|---|---|---|
| EP | 0865800 | 9/1998 |
| WO | 2007140597 | 12/2007 |

(Continued)

OTHER PUBLICATIONS

Eisele Article—David W. Eisele, MD et al., "Tongue neuromuscular and direct hypoglossal nerve stimulation for obstructive sleep apnea," Otolaryngologic Clinics of North America, Otolayngol Clin N Am 36 (2003) 501-510 (10 pages).

(Continued)

*Primary Examiner* — Brian T Gedeon
*Assistant Examiner* — Ankit Tejani
(74) *Attorney, Agent, or Firm* — Dicke, Billig & Czaja, PLLC

(57) ABSTRACT

An electrode cuff includes a first elongate portion and a second elongate portion. The first elongate portion is configured to removably contact a length of a nerve while the second elongate portion extends outwardly at an angle relative to a first side edge of the first elongate portion to at least partially wrap about the nerve. The electrode cuff includes a first series of electrodes that is spaced apart longitudinally along the first elongate portion. A width of the second elongate portion is sized to fit between adjacent branches extending from a nerve.

16 Claims, 7 Drawing Sheets

(56) References Cited

U.S. PATENT DOCUMENTS

| | | |
|---|---|---|
| 5,344,438 A | 9/1994 | Testerman |
| 5,351,394 A | 10/1994 | Weinberg |
| 5,398,596 A | 3/1995 | Fond |
| 5,400,784 A | 3/1995 | Durand et al. |
| 5,487,756 A | 1/1996 | Kallesoe et al. |
| 5,505,201 A | 4/1996 | Grill, Jr. et al. |
| 5,531,778 A | 7/1996 | Maschino |
| 5,540,734 A | 7/1996 | Zabara |
| 5,591,216 A | 1/1997 | Testerman et al. |
| 5,634,462 A | 6/1997 | Tyler et al. |
| 5,741,319 A | 4/1998 | Woloszko et al. |
| 5,824,027 A | 10/1998 | Hoffer et al. |
| 5,938,596 A | 8/1999 | Woloszko et al. |
| 6,015,389 A | 1/2000 | Brown |
| 6,041,780 A | 3/2000 | Richard |
| 6,093,197 A | 7/2000 | Bakula et al. |
| 6,366,815 B1 | 4/2002 | Haugland |
| 6,456,866 B1 | 9/2002 | Tyler et al. |
| 6,587,725 B1 | 7/2003 | Durand et al. |
| 6,600,956 B2 | 7/2003 | Maschino |
| 6,647,289 B2 | 11/2003 | Prutchi |
| 6,651,652 B1 | 11/2003 | Ward |
| 6,904,320 B2 | 6/2005 | Park et al. |
| 6,907,293 B2 | 6/2005 | Grill |
| 6,907,295 B2 | 6/2005 | Gross |
| 6,928,324 B2 | 8/2005 | Park |
| 6,978,171 B2 | 12/2005 | Goetz |
| 7,054,692 B1 | 5/2006 | Whitehurst et al. |
| 7,065,410 B2 | 6/2006 | Bardy et al. |
| 7,082,331 B1 | 7/2006 | Park |
| 7,082,336 B2 | 7/2006 | Ransbury et al. |
| 7,087,053 B2 | 8/2006 | Vanney |
| 7,117,036 B2 | 10/2006 | Florio |
| 7,128,717 B1 | 10/2006 | Thatch |
| 7,149,573 B2 | 12/2006 | Wang |
| 7,160,255 B2 | 1/2007 | Saadat |
| 7,200,440 B2 | 4/2007 | Kim |
| 7,248,930 B1 | 7/2007 | Woloszko et al. |
| 7,366,572 B2 | 4/2008 | Heruth |
| 7,395,119 B2 * | 7/2008 | Hagen et al. .......... 607/116 |
| 7,463,928 B2 | 12/2008 | Lee |
| 7,463,934 B2 | 12/2008 | Tronnes et al. |
| 7,473,227 B2 | 1/2009 | Hsu |
| 7,499,742 B2 * | 3/2009 | Bolea et al. .......... 600/372 |
| 7,591,265 B2 | 9/2009 | Lee |
| 7,596,413 B2 | 9/2009 | Libbus |
| 7,596,414 B2 | 9/2009 | Whitehurst |
| 7,630,771 B2 | 12/2009 | Cauller |
| 7,634,315 B2 | 12/2009 | Cholette |
| 7,644,714 B2 | 1/2010 | Atkinson et al. |
| 7,662,105 B2 | 2/2010 | Hatlestad |
| 7,672,728 B2 | 3/2010 | Libbus |
| 7,680,538 B2 | 3/2010 | Durand et al. |
| 7,717,848 B2 | 5/2010 | Heruth |
| 7,734,340 B2 | 6/2010 | DeRidder |
| 7,747,323 B2 | 6/2010 | Libbus |
| 7,751,880 B1 | 7/2010 | Cholette |
| 7,783,353 B2 | 8/2010 | Libbus |
| 7,787,959 B1 | 8/2010 | Morgan |
| 7,809,442 B2 | 10/2010 | Bolea et al. |
| 7,818,063 B2 | 10/2010 | Wallace |
| 2001/0010010 A1 | 7/2001 | Richmond et al. |
| 2002/0010495 A1 | 1/2002 | Freed et al. |
| 2002/0049479 A1 | 4/2002 | Pitts |
| 2002/0156507 A1 | 10/2002 | Lindenthaler |
| 2003/0093128 A1 | 5/2003 | Freed et al. |
| 2003/0114895 A1 | 6/2003 | Gordon et al. |
| 2003/0114905 A1 | 6/2003 | Kuzma |
| 2003/0195571 A1 | 10/2003 | Burnes et al. |
| 2003/0216789 A1 | 11/2003 | Deem et al. |
| 2004/0073272 A1 | 4/2004 | Knudson et al. |
| 2004/0111139 A1 | 6/2004 | McCreery |
| 2005/0004610 A1 | 1/2005 | Kim |
| 2005/0010265 A1 | 1/2005 | Baru Fassio |
| 2005/0085865 A1 | 4/2005 | Tehrani |
| 2005/0085866 A1 | 4/2005 | Tehrani |
| 2005/0085868 A1 | 4/2005 | Tehrani |
| 2005/0085869 A1 | 4/2005 | Tehrani |
| 2005/0101833 A1 | 5/2005 | Hsu |
| 2005/0165457 A1 | 7/2005 | Benser |
| 2005/0209513 A1 | 9/2005 | Heruth |
| 2005/0209643 A1 | 9/2005 | Heruth |
| 2005/0234523 A1 | 10/2005 | Levin |
| 2005/0261747 A1 | 11/2005 | Schuler |
| 2005/0267380 A1 | 12/2005 | Poezevara |
| 2005/0277844 A1 | 12/2005 | Strother |
| 2005/0277999 A1 | 12/2005 | Strother |
| 2005/0278000 A1 | 12/2005 | Strother |
| 2006/0030919 A1 | 2/2006 | Mrva et al. |
| 2006/0058852 A1 | 3/2006 | Koh |
| 2006/0064029 A1 | 3/2006 | Arad |
| 2006/0079802 A1 | 4/2006 | Jensen |
| 2006/0095088 A1 | 5/2006 | DeRidder |
| 2006/0103407 A1 | 5/2006 | Kakizawa et al. |
| 2006/0135886 A1 | 6/2006 | Lippert |
| 2006/0142815 A1 | 6/2006 | Tehrani |
| 2006/0167497 A1 | 7/2006 | Armstrong |
| 2006/0184204 A1 | 8/2006 | He |
| 2006/0195170 A1 | 8/2006 | Cohen |
| 2006/0247729 A1 | 11/2006 | Tehrani |
| 2006/0259079 A1 | 11/2006 | King |
| 2006/0266369 A1 | 11/2006 | Atkinson et al. |
| 2006/0271137 A1 | 11/2006 | Stanton-Hicks |
| 2006/0282127 A1 | 12/2006 | Zealear |
| 2006/0293720 A1 | 12/2006 | DiLorenzo |
| 2006/0293723 A1 | 12/2006 | Whitehurst |
| 2007/0021785 A1 | 1/2007 | Inman |
| 2007/0027482 A1 | 2/2007 | Parnis |
| 2007/0038265 A1 | 2/2007 | Tcheng |
| 2007/0043411 A1 | 2/2007 | Foster |
| 2007/0129780 A1 | 6/2007 | Whitehurst et al. |
| 2007/0233204 A1 | 10/2007 | Lima et al. |
| 2007/0239243 A1 | 10/2007 | Moffitt et al. |
| 2007/0255379 A1 | 11/2007 | Williams et al. |
| 2008/0046055 A1 | 2/2008 | Durand et al. |
| 2008/0103545 A1 | 5/2008 | Bolea et al. |
| 2008/0103570 A1 | 5/2008 | Gerber |
| 2008/0132987 A1 | 6/2008 | Westlund et al. |
| 2008/0172101 A1 | 7/2008 | Bolea et al. |
| 2008/0172116 A1 | 7/2008 | Mrva et al. |
| 2008/0177348 A1 | 7/2008 | Bolea et al. |
| 2008/0319506 A1 | 12/2008 | Cauller |
| 2009/0099439 A1 * | 4/2009 | Barolat .......... 600/372 |
| 2009/0210042 A1 * | 8/2009 | Kowalczewski .......... 607/118 |
| 2009/0308395 A1 | 12/2009 | Lee |
| 2009/0326408 A1 | 12/2009 | Moon |
| 2010/0094379 A1 | 4/2010 | Meadows et al. |
| 2010/0125310 A1 | 5/2010 | Wilson |
| 2010/0137931 A1 | 6/2010 | Hopper |
| 2010/0145221 A1 * | 6/2010 | Brunnett et al. .......... 600/554 |
| 2010/0152553 A1 | 6/2010 | Ujhazy |
| 2010/0174341 A1 | 7/2010 | Bolea et al |
| 2010/0198103 A1 | 8/2010 | Meadows et al. |
| 2010/0228133 A1 | 9/2010 | Averina |
| 2010/0228317 A1 | 9/2010 | Libbus |
| 2010/0241195 A1 | 9/2010 | Meadows et al. |

FOREIGN PATENT DOCUMENTS

| | | |
|---|---|---|
| WO | 2008025155 | 3/2008 |
| WO | 2008048471 | 4/2008 |
| WO | 2009048580 | 4/2009 |
| WO | 2009048581 | 4/2009 |
| WO | 2009135138 | 11/2009 |
| WO | 2009135140 | 11/2009 |
| WO | 2009135142 | 11/2009 |
| WO | 2009140636 | 11/2009 |
| WO | 2010039853 | 4/2010 |
| WO | 2010059839 | 5/2010 |

(56) References Cited

FOREIGN PATENT DOCUMENTS

| WO | 2010117810 | 10/2010 |
|---|---|---|
| WO | 2011112843 | 9/2011 |

OTHER PUBLICATIONS

Goodall Article—Eleanor V. Goodhall et al., "Position-Selective Activation of Peripheral Nerve Fibers with a Cuff Electrode," IEEE Transaction on Biomedical Engineering, vol. 43, No. 8, Aug. 1996, pp. 851-856.

Oliven Article—Arie Oliven et al., "Upper airway response to electrical stimulation of the genioglossus in obstructive sleep apnea," Journal of Applied Physiology, vol. 95, pp. 2023-2029, Nov. 2003, www.jap.physiology.org on Sep. 18, 2006. (8 pages).

Schwartz Article—Alan R. Schwartz MD et al., Theraputic Electrical Stimulation of the Hypoglossal Nerve in Obstructive Sleep Apnea, Arch Otolaryngol Head And Neck Surg., vol. 127, Oct. 2001, pp. 1216-1223. Copyright 2001 American Medical Association. (8 pages).

PARK Article—"Preoperative Percutaneous Cranial Nerve Mapping in Head and Neck Surgery," ARCH Facial Plast Surg/vol. 5, Jan./Feb. 2003, www.archfacial.compages 86-91.

Naples Article—Gregory G. Naples et al., "A Spiral Nerve Cuff Electrode for Peripheral Nerve Stimulation," 8088 IEEE Transactions on Biomedical Engineering, 35. Nov. 1988, No. 11, New York, NY, pp. 905-915.

\* cited by examiner

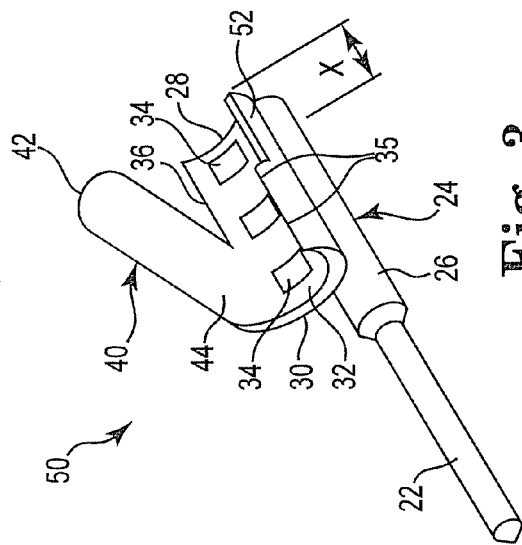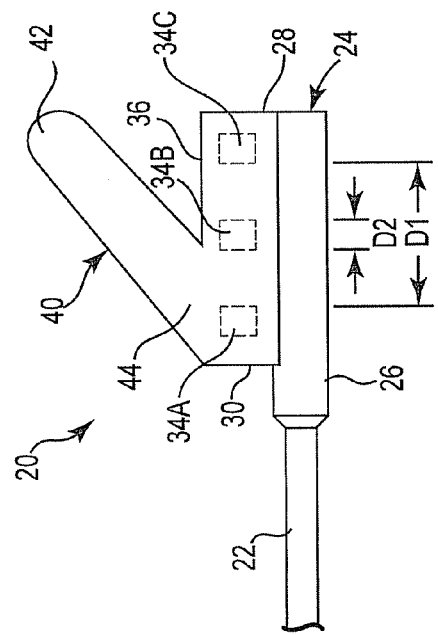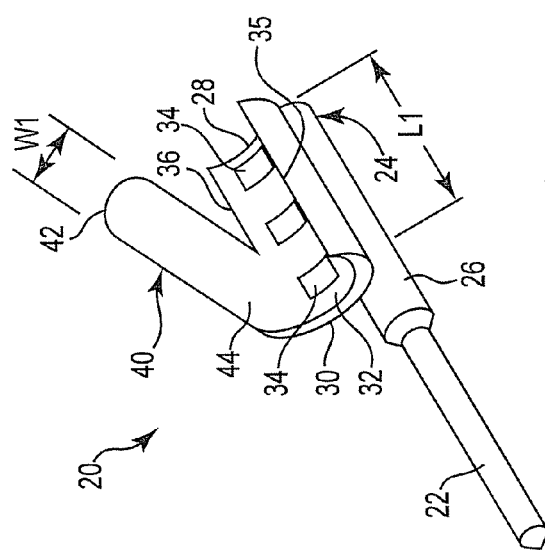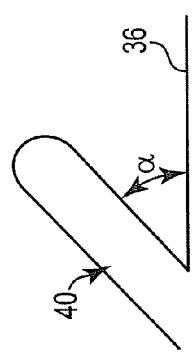

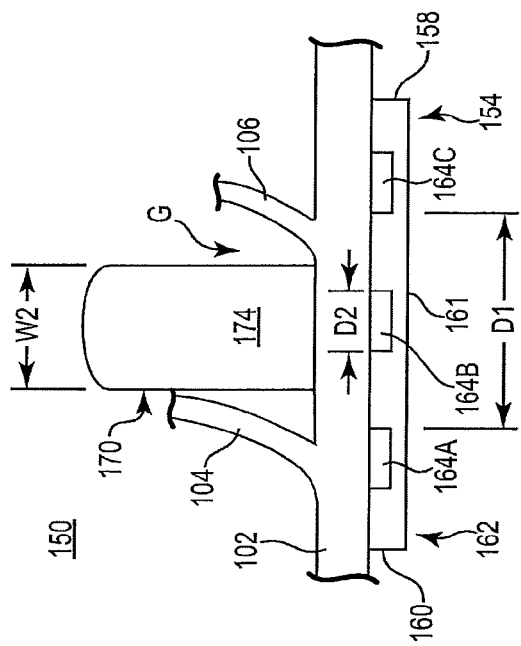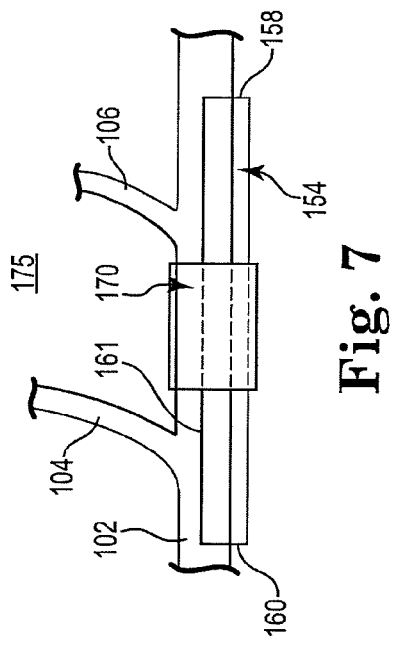

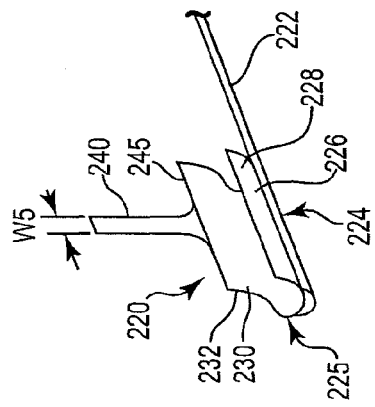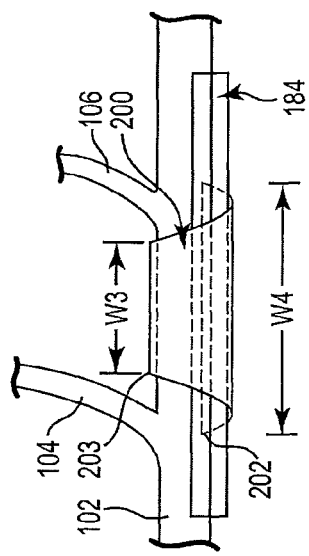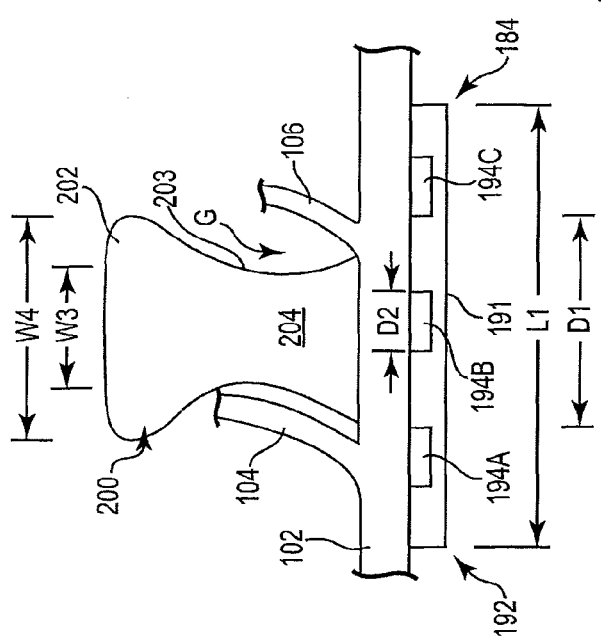

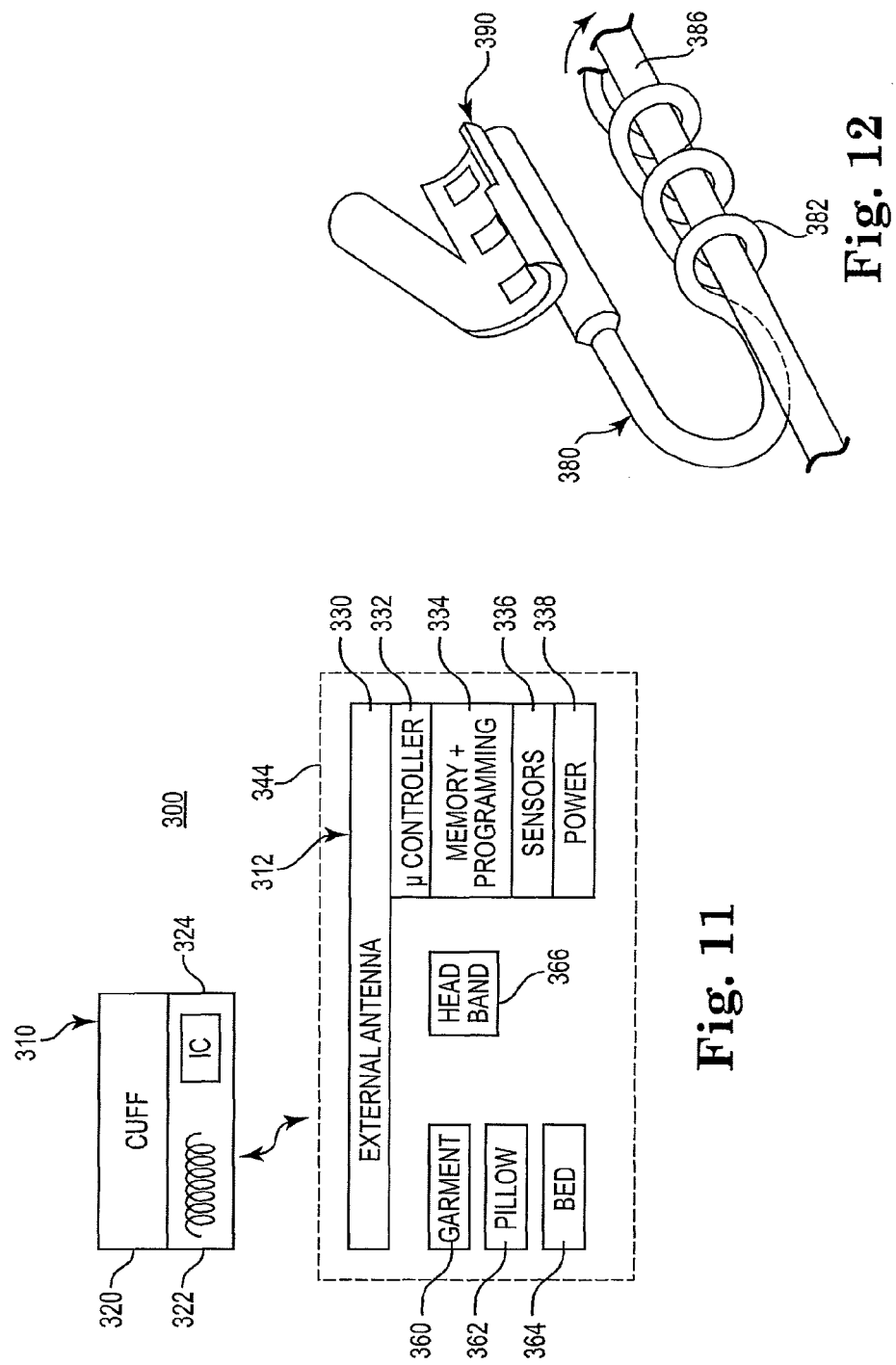

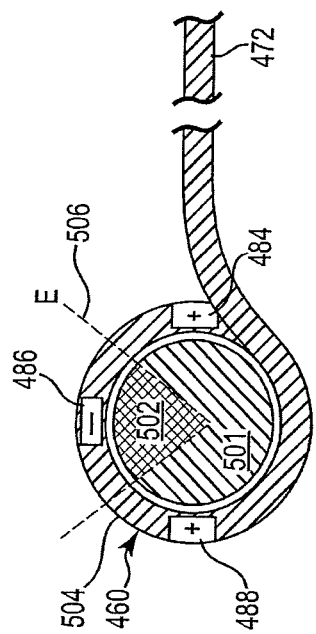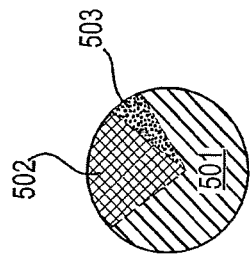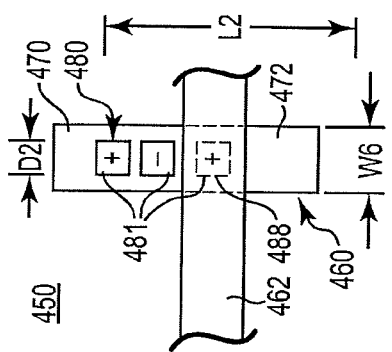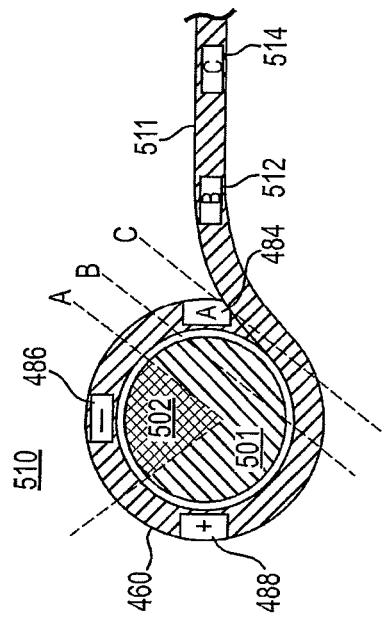
Fig. 13
Fig. 14
Fig. 15
Fig. 16

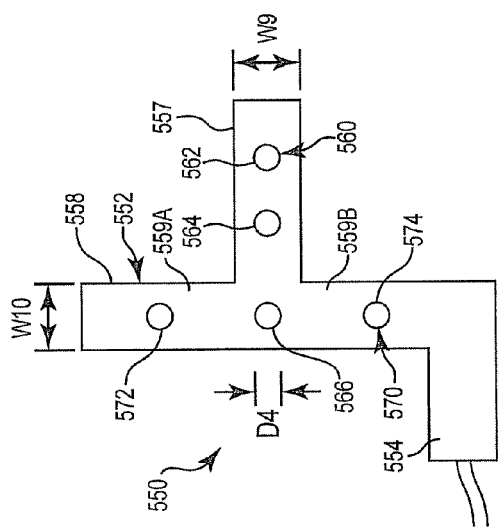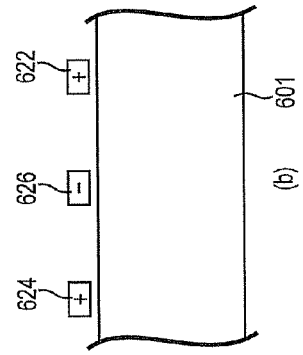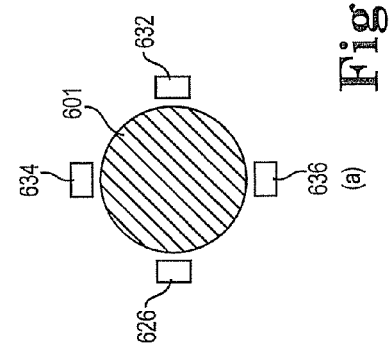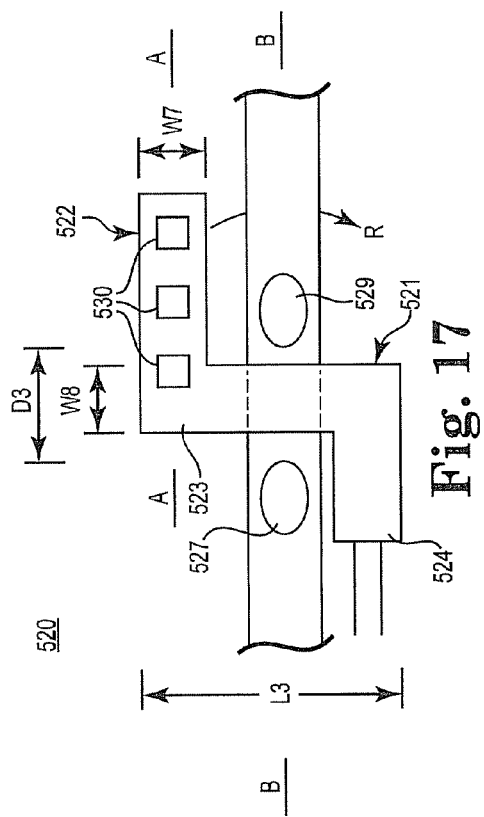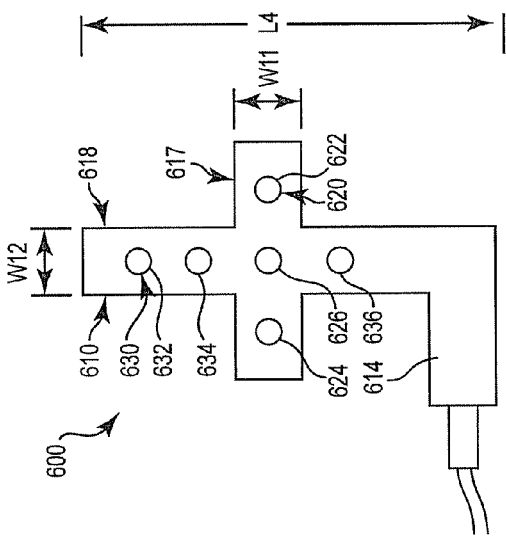

US 8,934,992 B2

NERVE CUFF

CROSS-REFERENCE TO RELATED APPLICATION

This application is a Non-Provisional Application of Provisional U.S. Patent Application Ser. No. 61/530,002, entitled "Nerve Cuff," filed Sep. 1, 2011, incorporated herein by reference.

BACKGROUND

A forced contraction of a muscle can be caused via electrical stimulation of a nerve that innervates the muscle. Typically, a power source is coupled to the nerve via an electrical stimulation lead that is, in turn, coupled to the nerve. For example, a distal end of an electrical stimulation lead is formed as a cuff that can be secured about the nerve to orient an electrically conductive portion of the lead in direct contact with the nerve. However, in many instances, the location in which a particular nerve resides presents significant challenges in maneuvering the distal conductive portion of the electrical lead into a target position relative to the nerve and in securing the distal conductive portion in the target position.

BRIEF DESCRIPTION OF THE DRAWINGS

FIG. 1 is a perspective view schematically illustrating a nerve electrode cuff system, according to an example of the present disclosure.

FIG. 1B is a diagram schematically illustrating an aspect of a nerve electrode cuff system, according to an example of the present disclosure.

FIG. 2 is a top plan view schematically illustrating a nerve electrode cuff system, according to an example of the present disclosure.

FIG. 3 is a perspective view schematically illustrating a nerve electrode cuff system, according to an example of the present disclosure.

FIG. 6 is a front plan view schematically illustrating an aspect of implanting a nerve electrode cuff system, according to an example of the present disclosure.

FIG. 7 is a front plan view schematically illustrating an aspect of implanting a nerve electrode cuff system, according to an example of the present disclosure.

FIG. 8 is a front plan view schematically illustrating an aspect of implanting a nerve electrode cuff system, according to an example of the present disclosure.

FIG. 9 is a front plan view schematically illustrating an aspect of implanting a nerve electrode cuff system, according to an example of the present disclosure.

FIG. 10 is a perspective view schematically illustrating a nerve electrode cuff system, according to an example of the present disclosure.

FIG. 11 is a block diagram schematically illustrating a nerve stimulation system, according to an example of the present disclosure.

FIG. 12 is a perspective view schematically illustrating a nerve electrode cuff system, according to an example of the present disclosure.

FIG. 13 is a front plan view schematically illustrating a nerve electrode cuff system, according to an example of the present disclosure.

FIGS. 14-15 are sectional views schematically illustrating a nerve electrode cuff, according to an example of the present disclosure.

FIG. 16 is a sectional view schematically illustrating a nerve in relation to application of a nerve electrode cuff system, according to an example of the present disclosure.

FIG. 17 is a top plan view schematically illustrating a nerve electrode cuff juxtaposed with a nerve, according to an example of the present disclosure.

FIG. 18 is a top plan view schematically illustrating a nerve electrode cuff, according to an example of the present disclosure.

FIG. 19 is a top plan view schematically illustrating a nerve electrode cuff, according to an example of the present disclosure.

FIG. 20 is a diagram, including a sectional view and a side view, schematically illustrating a nerve electrode cuff implanted relative to a nerve, according to an example of the present disclosure.

DETAILED DESCRIPTION

Figure 4:
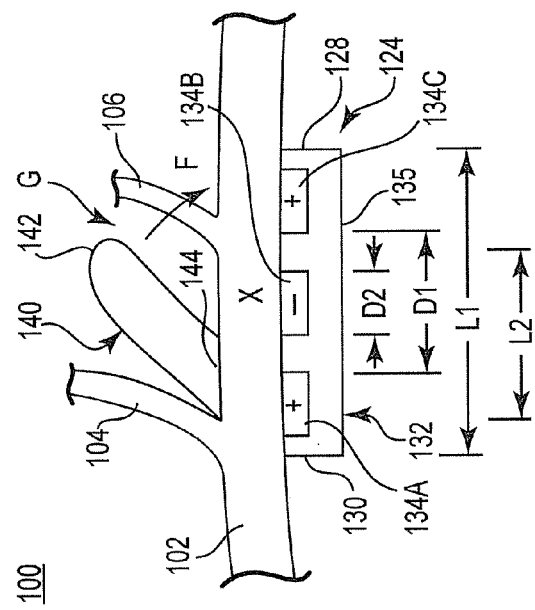
FIG. 4 is a front plan view schematically illustrating an aspect of implanting a nerve electrode cuff system, according to an example of the present disclosure.

In the following Detailed Description, reference is made to the accompanying drawings which form a part hereof, and in which is shown by way of illustration specific embodiments of the present disclosure which may be practiced. In this regard, directional terminology, such as "top," "bottom," "front," "back," "leading," "trailing," etc., is used with reference to the orientation of the Figure(s) being described. Because components of embodiments of the present disclosure can be positioned in a number of different orientations, the directional terminology is used for purposes of illustration and is in no way limiting. It is to be understood that other embodiments may be utilized and structural or logical changes may be made without departing from the scope of the present disclosure.

Embodiments of the present disclosure are directed to nerve cuff assemblies adapted for ease of use and for secure implantation of a stimulation lead in a nerve stimulation system. In one embodiment, these nerve cuff assemblies are adapted for use in implantation relative to a hypoglossal nerve as part of a system and method of treating sleep disordered breathing, such as obstructive sleep apnea. In one aspect, these embodiments are configured to produce consistent, repeatable surgical implantation and robust coupling to a nerve. In another aspect, these embodiments are configured for implantation on a more distal portion of a hypoglossal nerve in which, in some instances, the nerve cuff will be located in proximity to one or more nerves branching off the main trunk of the hypoglossal nerve. In this regard, the particular features of the respective nerve cuff assemblies accommodate placement among such nerve branches.

These embodiments, and additional embodiments, are described and illustrated in detail in association with FIGS. 1A-20.

FIG. 1A is a perspective view schematically illustrating an electrical lead 20, including a lead body 22 and a distal cuff portion 24, according to an embodiment of the present disclosure. In one embodiment, distal cuff portion 24 includes a spine portion 26 that extends from lead body 22, and which supports a cuff body 32 defining a first elongate portion. The cuff body 32 includes a distal end 28 and a proximal end 30 and a series of electrodes 34A, 34B, 34C extending therebetween to be spaced apart longitudinally along a length of the cuff body 32. In some embodiments, distal cuff portion 24 additionally includes a flap 40, defining a second elongate portion and having a distal end 42 (e.g. a tip) and a base 44 that extends from one side edge 36 of cuff body 32. In one embodiment, flap 40 extends outwardly from the side edge 36 of cuff body 32 to form a generally acute angle (α) relative to side edge 36 of the cuff body 32, as shown in FIG. 1B. In one embodiment, the angle (α) can fall within a range of about 10 to about 80 degrees, and in other embodiments, the angle (α) falls within a range of about 30 to about 60 degrees. In some embodiments, the angle (α) falls within a range of about 40 to about 50 degrees. In one embodiment, the angle (α) is about 45 degrees. In one aspect, the angle (α) is selected to orient the flap 40 to be interposed between two adjacent nerve branches and to wrap in contact about cuff body 32, as will be further shown in FIGS. 4-5. In another aspect, base 44 of flap 40 is positioned at a proximal end 30 of cuff body 32 so that distal portion 42 is oriented toward distal end 28 of cuff body 32.

It will be understood that in other embodiments, base 44 of flap 40 can be attached to distal end 28 of cuff body 32 so that flap 40 extends toward proximal end 30 of cuff body at an angle (α). In other words, the flap 40 would extend in direction opposite that shown in FIG. 1A.

FIG. 2 is a side plan view further schematically illustrating the lead 20 of FIG. 1. In one example, as shown in FIG. 2, two outer electrodes 34A, 34C are spaced apart from each other along a length of the cuff body 32 by a distance D1 and each electrode (e.g. electrode 34B) has a width (D2). In one example, the width W1 of the flap 40 (FIG. 1A) is generally equal to or greater than the width (D2) of the central electrode 34B but the width (W1) of flap 40 is less than the distance of separation (D1) between the two outer electrodes 34A, 34C. In this arrangement, flap 40 exhibits a narrow profile for fitting between adjacent nerve branches 104, 106, as depicted in at least FIGS. 4-5.

In some examples, the width W1 of flap 40 is twice the width (D2) of one of the respective electrodes (e.g. electrode 34B). In other examples, the width W1 of flap 40 is three times the width (D2) of one of the respective electrodes (e.g. electrode 34B). In one aspect, by making flap 40 generally wider than a respective electrode (e.g. electrode 34B) a sufficient overlap of the flap 40 relative to the electrode (e.g. electrode 34B) is obtained.

FIG. 3 is a perspective view schematically illustrating a lead 50 having substantially the same features and attributes as lead 20 (FIG. 1), except with side edge 35 of cuff body 32 including a notched portion 52, according to an embodiment of the present disclosure. In one embodiment, the notched portion 52 begins at the distal end 28 and, in some embodiments, extends a distance (X) that is about one-quarter to one-third of a length (L1) of the cuff body 32, as shown in FIG. 3. The notched portion 52 is positioned and sized to permit a distal portion 42 of flap 40 to extend within notched portion 52 upon flap 42 being wrapped around a nerve (as shown in FIGS. 4-5) so that flap 40 retains a smaller profile when fully secured about nerve.

In other embodiments, notched portion 52 is located at a midportion of cuff body 32 or located at a proximal end 30, such as the previously mentioned embodiment in which a flap 40 would extend from a distal end 28 of the cuff body toward the proximal end 30.

In one embodiment, flap 40 is biased in a curled shape approximating the outer circumference of a nerve so that when flap 40 is released (from being held via forceps or other means), flap 40 automatically wraps about the nerve and distal portion 42 automatically falls within notch portion 52 of cuff body 32. In another aspect, notched portion 52 is sized and positioned based on the angle (α) at which flap 40 extends (FIG. 1B) to ensure that distal portion 42 of flap 40 aligns with notched portion 52.

Figure 5:
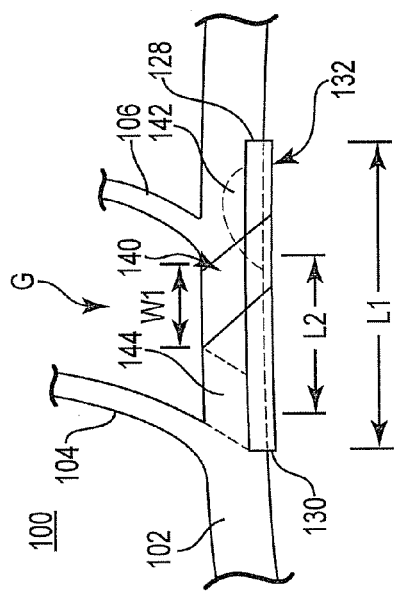
FIG. 5 is a front plan view schematically illustrating an aspect of implanting a nerve electrode cuff system, according to an example of the present disclosure.

FIG. 4 is a diagram 100 schematically illustrating implantation of an electrode cuff 124 about a nerve 102, according to an embodiment of the present disclosure. In one embodiment, electrode cuff 124 includes substantially the same features and attributes as electrode lead 20 (FIGS. 1-3) with similar reference numerals referring to similar elements. It will be understood that a lead body, such as lead body 22, extending proximally from cuff 124 but is not shown for illustrative purposes.

As shown in FIG. 4, upon partial implantation, the cuff body 132 lies underneath nerve 102 and is positioned along a length of nerve 102 so that flap 140, when wrapped about nerve 102 (as represented by directional arrow F), will pass through the gap G between branch nerves 104, 106. In one embodiment, flap 140 has width (W1 in FIG. 1) less than a width of the gap (represented by length L2 in FIG. 4) between the branch nerves 104, 106. In one embodiment, the width (W1) of flap 140 is substantially less than a length (L1 in FIG. 4) of the cuff body 132. In one embodiment, the electrodes 134A, 134B, 134C provide a tripolar arrangement with a negative electrode (e.g. cathode) interposed between two positive electrodes (e.g. anodes), although it will be understood that other electrode configurations can be used. As shown in FIG. 4, the target zone for stimulation is generally represented by the marker "X" shown along nerve 102. Accordingly, when the target zone for stimulation of the nerve falls within an area encroached by branch nerves 104, 106, the nerve cuff 124 is especially suited to being secured relative to nerve 102 despite the presence of the branch nerves 104, 106 adjacent the target zone (represented by X). In particular, the relatively narrow width of flap 40 enables its positioning between branch nerves 104, 106 while the angle (α) at which flap 40 extends from the proximal end 130 of the cuff body 132 further facilitates interposing the flap 40 between branch nerves 104, 160 and the self-wrapping behavior of flap 40 about cuff body 132 and nerve 102.

In one example, as shown in FIG. 4, two outer electrodes 134A, 134C are spaced apart from each other along a length of the cuff body 132 by a distance D1 and each electrode (e.g. electrode 134B) has a width (D2). In one example, the width W1 of the flap 140 (such as W1 of flap 40 in FIG. 1A) is generally equal to or greater than the width (D2) of the central electrode 134B but width (W1) is less than the distance of separation (D1) between the two outer electrodes 134A, 134C. In this arrangement, flap 140 exhibits a narrow profile for fitting between adjacent nerve branches 104, 106.

In some examples, the width W1 of flap 140 is twice the width (D2) of one of the respective electrodes (e.g. electrode 134B). In other examples, the width W1 of flap 140 is three times the width (D2) of one of the respective electrodes (e.g. electrode 134B).

As shown in FIG. 5, upon guiding flap 140 through gap G and then permitting flap 40 to wrap itself about cuff body 132, the cuff body 132 becomes releasably secured about nerve 102. Moreover, because flap 140 straddles the gap G between the two branch nerves 104, 106, the cuff body 132 is further restrained from longitudinal movement along the length of nerve 102.

As apparent from FIG. 5, in one example flap 140 defines a first elongate portion having a length sufficient to extend from one side edge of the cuff body 132, encircle the nerve, and overlap at least a portion of the opposite side edge of the cuff body 132.

FIG. 6 is a diagram 150 including a side plan view schematically illustrating implantation of an electrode cuff 154 about a nerve 102, according to an embodiment of the present disclosure. As shown in FIG. 6, flap 170 includes a base 174 mounted to or extending from a midportion 161 (intermediate between distal end 158 and proximal end 160) of cuff body 162. Accordingly, with cuff body 162 positioned along a length of nerve 102 to place electrodes 164 at a desired target portion of nerve 102, flap 170 is sized with a width (W2) configured to be interposed between branch nerves 104, 106. However, unlike the angled flap 40 (FIG. 1-5), flap 170 extends generally perpendicular to the longitudinal axis of the cuff body 162. FIG. 7 schematically illustrates the arrangement upon flap 170 being wrapped about nerve 102 and the cuff body 162 to secure electrode cuff 154 about nerve 102. Accordingly, the embodiment of FIGS. 6-7 includes substantially the same features and attributes as the embodiment of FIGS. 1-5, except for flap 170 being mounted relative to a midportion 161 of cuff body 162 and for flap 170 being generally perpendicular to cuff body 162.

In one example, as shown in FIG. 6, two outer electrodes 164A, 164C are spaced apart from each other along a length of the cuff body 162 by a distance D1 and each electrode (e.g. electrode 164B) has a width (D2). In one example, the width W2 of the flap 170 is generally equal to or greater than the width (D2) of the central electrode 164B but width (W2) is less than the distance of separation (D1) between the two outer electrodes 164A, 164C. In this arrangement, flap 170 exhibits a narrow profile for fitting between adjacent nerve branches 104, 106.

In some examples, the width W1 of flap 170 is twice the width (D2) of one of the respective electrodes (e.g. electrode 164B). In other examples, the width W1 of flap 170 is three times the width (D2) of one of the respective electrodes (e.g. electrode 164B). In one aspect, by making flap 170 generally wider than a respective electrode (e.g. electrode 164B) a sufficient overlap of the flap 170 relative to the electrode (e.g. electrode 164B) is obtained.

FIG. 8 is a diagram schematically illustrating an electrode cuff 184 being implanted about nerve 102 using flap 200, according to an embodiment of the present disclosure. Electrode cuff 184 includes substantially the same features and attributes as electrode cuff 154 as previously described in association with FIGS. 6-7, except with flap 200 having a tapered shape. As shown in FIG. 8, like flap 170 of electrode cuff 154 of FIG. 6, flap 200 of electrode cuff 184 has a base 204 mounted at a midportion 191 of cuff body 192. However, unlike the generally straight flap 170, flap 190 includes a butterfly-type shape in which a waist portion 203 of flap 200 is substantially narrower than the base 204 and/or the distal portion 202 of flap 200. In one aspect, waist portion 203 has a width (W3) substantially less than a width (W4) of the distal portion 202 or base 204 of flap 190. In one embodiment, waist portion 203 is at an intermediate location between the distal portion 202 and base portion 204. In one aspect, width (W3) of waist portion 203 is less than distance (gap G) between the branch nerves 104, 106. In one embodiment, distal portion 202 and base portion 204 have a width (W4) that is substantially less than a length (L1) of cuff body 192.

In one aspect, by making the distal portion 202 and the base portion 204 substantially wider than the waist portion 203, the flap 200 has a substantially greater surface area in contact with nerve 102 and with cuff body 192 as flap 200 wraps around those structures, which in turn, increases the holding strength the flap 190 relative to those structures. In addition, in another aspect, by providing generally wider portions 202 and 204 of flap 200 on opposite sides of the gap (G) between the branch nerves 104, 106, and sizing the waist portion 203 to fit between branch nerves 104, 106, the electrode cuff 184 becomes more securely anchored along the length of the nerve 102 (less likely to slide) and becomes more resistant to shifting/twisting.

In other embodiments, width (W4) of distal portion 202 and/or base portion 204 is generally equal to a length (L1) of cuff body 132 even while the waist portion 193 has width (W3) that remains sized to fit in the gap G between branch nerves 104, 106.

In one example, as shown in FIG. 8, two outer electrodes 194A, 194C are spaced apart from each other along a length of the cuff body 192 by a distance D1 and each electrode (e.g. electrode 194B) has a width (D2). In one example, the width W3 of the narrower waist portion 203 of flap 200 is generally equal to or greater than the width (D2) of the central electrode 194B but width (W3) is less than the distance of separation (D1) between the two outer electrodes 194A, 194C. In this arrangement, narrower waist portion 203 of flap 200 exhibits a narrow profile for fitting between adjacent nerve branches 104, 106.

In some examples, the width W3 of waist portion 203 is twice the width (D2) of one of the respective electrodes (e.g. electrode 194B). In other examples, the width W3 of waist portion 203 is three times the width (D2) of one of the respective electrodes (e.g. electrode 194B). In one aspect, by making flap 200 generally wider than a respective electrode (e.g. electrode 194B) a sufficient overlap of the flap 200 relative to the electrode (e.g. electrode 194B) is obtained.

FIG. 9 is diagram including a side plan view schematically illustrating the flap 200 of cuff 184 of FIG. 8 when completely wrapped about the cuff body 192 and nerve 102.

FIG. 10 is a perspective view schematically illustrating an electrode lead 220, according to an embodiment of the present disclosure. As shown in FIG. 10, electrode lead 220 includes a lead body 222 and an electrode cuff 224. The cuff 224 includes cuff body 225 having a short flap portion 226 on a first side 228 and a long flap portion 230 on a second opposite side 232 of the cuff body 225. In one aspect, the long flap portion 230 is substantially longer (in a direction generally perpendicular to a longitudinal axis of the lead body 202) than the short flap portion 226. In addition, an elongate strap 240 extends from a side edge 245 of the long flap portion 230. The elongate strap 240 is sized and positioned to help guide the long flap portion 230 behind a nerve during surgery. In one embodiment, elongate strap 240 has a width (W5) that is substantially less than a length of long flap portion 230 and of the cuff body 225 in general.

FIG. 11 is a diagram 300 schematically illustrating a stimulation system 300, according to an embodiment of the present disclosure. As shown in FIG. 11, system 300 includes an implantable cuff module 310 and an external support module 312. The implantable cuff module 310 includes a cuff 320, an antenna 322, and an integrated circuit 324. In one embodiment, cuff 320 includes any one of the cuff designs described within the present disclosure as well as other cuff designs. In one embodiment, the antenna 322 comprises a radiofrequency (RF) antenna for performing wireless communication with a reciprocating antenna or circuitry.

The external support module 312 includes an external antenna 330 (external to the body in which cuff module 310 is implanted), microcontroller 332, memory and programming element 334, sensor array 336, and power unit 338.

The external antenna 330 is equipped to perform wireless communication via RF waves or using other wireless communication protocols. Microcontroller 332 directs operation of the cuff module 310 and various components of the support module 312. Memory and programming element 334 stores a therapy regimen and stimulation control profiles for electrode cuff 322. Sensor array 336 includes one or more sensors placed and configured to detect physiologic parameters relating to respiration and general indicators of health in order to detect obstructed breathing patterns and/or whether or not an efficacious response has occurred as a result of therapy applied via system 300. In some embodiments, the sensors 336 sense information regarding acoustic parameters, position/posture of a patient, heart rate, bioimpedance, blood oxygenation, respiratory rate, inspiratory and expiratory phases, etc.

In one embodiment, as represented by dashed lines 344, the components and elements of external support module 312 are housed in one or more containing elements. In some embodiments, the containing elements include one or more of a garment 360, pillow 362, bed 364, and headband 366. In one aspect, the garment 360 includes one or more of a shirt, pants, necklace, wristband, and/or sleeve or other article that can be worn on the body and is constructed to house one or more of the elements of the external support module 312 in relatively close proximity to the implanted cuff module 310 to enable wireless communication between the cuff module 310 and the external support module 312. In one aspect, by housing power unit 338 in garment 360, the patient avoids having a power unit implanted in their body. The garment 360 is sized and shaped so that when the patient is sleeping while wearing garment 360, the power unit 338 becomes positioned in sufficiently close proximity to the implanted cuff module 310 to ensure proper communication and transmission of power to the cuff module 310.

FIG. 12 is perspective view schematically illustrating a lead system 380, according to an embodiment of the present disclosure, in which lead body 380 includes an anchor portion 382 secured to a nearby tendon or body structure, such as the digastric tendon 386. In one embodiment, anchor portion 382 forms a coiled or pigtail shape configured to automatically wrap itself about the tendon 386. In this way, cuff 390 becomes more securely attached in the vicinity of its implantation about a nerve 386. In one embodiment, the anchor portion 382 is implemented on a freestanding cuff module, such as cuff 390 in FIG. 12 or cuff module 310 in FIG. 11. In other embodiments, the anchor portion 382 is deployed on a full length lead that extends from a cuff module to an implanted pulse generator or controller.

FIG. 13 is a diagram 450 including a top plan view schematically illustrating an electrode cuff 460 aligned for deployment on a nerve 462, according to an embodiment of the present disclosure. The electrode cuff 460 includes a first end 470, a second end 472 with an array 480 of electrodes 481 aligned along a portion of cuff 460. As shown in FIG. 13, in one embodiment, the array 480 of electrodes 481 includes a first anode 484, a cathode 486, and second anode 488 with cathode 486 interposed between the respective anodes 484, 488.

In general terms, the electrode cuff 460 is configured for mounting on nerve 102 so that a longitudinal axis of the electrode array 480 is aligned generally perpendicular to a longitudinal axis of nerve 102 in the vicinity at which cuff 460 is deployed. In other words, instead of aligning a series of electrodes to extend along a length of nerve 102, the cuff 460 is sized and configured so that the series of electrodes extend circumferentially about a nerve and generally perpendicular to a longitudinal axis of the nerve 102.

In one embodiment, the electrode cuff 460 has a width (W6) and a length (L2) with length (L2) being substantially greater than width (W6). In one aspect, width (W6) is at least one-half the length (L2) with the width (W6) sized to fit between branch nerves (such as branch nerves 104, 106 in FIG. 4). Accordingly, electrode cuff 460 is suited for deployment in more distal regions of nerve and/or in regions in which tight spacing exists between adjacent branches from a nerve.

In one example, as shown in FIG. 13, electrodes 481 have a width (D2) and the width W6 of the cuff 460 is generally equal to or greater than the width (D2) of the electrodes 481. In some examples, the width W6 of cuff 460 is about twice the width (D2) of the electrodes 481. In other examples, the width W6 of cuff 460 is about three times the width (D2) of each electrode 481. In these arrangements, cuff 460 exhibits a narrow profile for fitting between adjacent nerve branches (such as nerve branches 104, 106 shown in FIGS. 4-5).

FIG. 14 is a sectional view of an elongate electrode cuff (such as cuff 460 in FIG. 13) deployed about a nerve 501, according to an embodiment of the disclosure. As shown in FIG. 14, with the array 480 of electrodes positioned about the circumference of the nerve 102 and upon applying an electrical stimulation signal to the nerve 501 via cuff 460, an energy field (represented by E within the boundaries 504 and 506) exerted upon nerve 501, which thereby causes firing of various fascicles within nerve 501 (as represented by region 502).

FIG. 15 is sectional view an elongate electrode cuff (such as cuff 460 in FIG. 13) deployed about a nerve 501, according to an embodiment of the disclosure. However, in this embodiment, a portion 511 of the electrode cuff 460 extends generally outward from the rest of the cuff 460 to orient additional electrodes at a spaced distance from the nerve and the other electrodes (488, 486) that are in contact with the nerve. In this arrangement, a controller is used to select whether electrode 484, 512, 514 is activated and depending upon which electrode 484, 512, 514 is activated, a different shape and size energy field will act on the nerve. In general terms, because the electrodes 512, 514 are spaced apart from the nerve 501, the energy field is expanded and stretched upon activation of one of those remotely located electrodes. As shown in FIG. 15, upon activation of electrode 484 along with electrodes (488, 486), the energy field takes the shape and size represented by region 502 as shown in FIGS. 14 and 15. However, if electrode 512 is activated instead of electrode 484, then one boundary of the energy field moves from dashed line A to B, and the resulting energy field takes on the size and shape depicted as the sum of regions 502 and 503 in FIG. 16. Similarly, if electrode 514 were activated instead of electrodes 484 or 512, then the energy field would be further expanded in size toward the "right" side of the nerve with the new boundary defined by dashed line C, shown in FIG. 15.

In one embodiment, cuff 410 is deployed so that the extended portion 511 extends toward a surface of the body.

In one aspect, the electrode cuff 460 is particularly adapted for mounting transversely to longitudinal axis of the nerve at the target stimulation location to fit between adjacent branch nerves. In addition, when additional electrodes such as electrodes 512 and 514 are incorporated into the cuff 410, an operator can selectively modify a shape and size of the energy field applied to a cross-section of the nerve to achieve the targeted stimulation.

FIG. 17 is a diagram 520 schematically illustrating an electrode lead 521 being mounted relative to a nerve, according to an embodiment of the present disclosure. As shown in FIG. 17, electrode lead 521 includes an electrode portion 522, a transverse portion 523, and a body portion 524. A longitudinal axis of the electrode portion 522 extends generally parallel to a longitudinal axis of the body portion 524. Meanwhile, the transverse portion 523 is interposed between, extends generally perpendicular to, the respective electrode and body portions 522, 524.

The electrode portion 522 includes an array of electrodes 530 aligned in series. The transverse portion 523 has length (L3) sufficient to extend about at least one-third to one-half of a circumference of the nerve and has a width (W8) sized to fit between adjacent branch nerves 527, 529 (see also 104, 106 in FIG. 3). In one aspect, branch nerves 527, 529 are spaced apart by a distance D3.

In one aspect, the transverse portion 523 is biased to self wrap partially about the circumference of the nerve which in turn aligns the electrode portion 522 generally parallel to a longitudinal axis of the nerve and for contact with the nerve in that alignment. Similarly, the transverse alignment of the transverse portion 523 also aligns body portion to extend alongside the nerve and to be further secured thereto.

FIG. 18 is a top plan view of an electrode cuff 550, according to an embodiment of the present disclosure. As shown in FIG. 18, electrode cuff 550 includes an electrode portion 552 and a body portion 554 from which the electrode portion 552 extends. The electrode portion 552 has a first electrode portion 557 and a second electrode portion 558. The first electrode portion 557 supports an array 560 including electrodes 562, 564, and 566 while the second electrode portion 558 supports a second electrode array 570 including electrodes 572, 574, and electrode 566. Accordingly, electrode 566 serves in both electrode arrays 560, 570 depending upon which electrode array 560, 570 is activated (or if both electrode arrays 560, 570 are activated). In another aspect, first electrode portion 557 (and its electrode array 560) extends generally perpendicular to second electrode portion 558 (and its electrode array 570). The first electrode portion 557 is sized and positioned for alignment generally parallel to a longitudinal axis of a nerve while the second electrode portion is sized and position for alignment transverse to the longitudinal axis of the nerve. In one embodiment, either the first end portion 559A or the second end portion 559B of the second electrode portion 558 is aligned to extend at least partially circumferentially about the nerve, such as between two adjacent branch nerves (such as branch nerves 527, 529 in FIG. 17). In another aspect, the second end portion 559B of second electrode portion 558 extends between the first electrode portion 557 and the body portion 554.

In one embodiment, second electrode portion 558 is sized and biased to self-wrap at least partially about a circumference of the nerve, which in turn aligns first electrode portion 557 to be generally parallel to a longitudinal axis of the nerve and for contact with the nerve in that alignment.

In one example, second electrode portion 558 has a width (W10) sized to fit between adjacent branch nerves 527, 529 (FIG. 17). Accordingly, the width W10 is less than the distance D3 between the adjacent nerve branches 527, 529. In one example, the width W10 is at least twice the width (or diameter) D4 of each electrode 566, 572, 574 and less than the distance D3. In another example, the width W10 is at least three times the width (or diameter) D4 of each electrode 566, 572, 574 and less than the distance D3.

FIG. 19 is a top plan view of an electrode cuff 600, according to an embodiment of the present disclosure. As shown in FIG. 18, electrode cuff 600 includes an electrode portion 610 and a body portion 614 from which the electrode portion 612 extends. The electrode portion 612 has a first electrode portion 617 and a second electrode portion 618. The first electrode portion 617 supports an array 620 including electrodes 622, 624, and 626 while the second electrode portion 618 supports a second electrode array 630 including electrodes 632, 634, 636 and electrode 626. Accordingly, electrode 626 serves in both electrode arrays depending upon which electrode array 620, 630 is activated (or if both electrode arrays 620, 630 are activated). In another aspect, first electrode portion 617 (and its electrode array 620) extends generally perpendicular to second electrode portion 618 (and its electrode array 630) with the respective first and second electrode portions 617, 618 forming a cross shape with electrode 626 in the center of the cross. The first electrode portion 617 is sized and positioned for alignment generally parallel to a longitudinal axis of a nerve while the second electrode portion 618 is sized and position for alignment transverse to the longitudinal axis of the nerve. In one embodiment, either the first end portion 619A or the second end portion 619B of the second electrode portion 618 is aligned to extend at least partially circumferentially about the nerve, such as between two adjacent branch nerves (such as branch nerves 527, 529 in FIG. 17).

In this arrangement, the second electrode portion 618 is sized and shaped to be interposed between a pair of adjacent branch nerves (such as nerves 104, 106 in FIGS. 4-5) and/or to fit between or among other structures surrounding the nerve, thereby ensuring quick and robust implantation of nerve cuff 610 about the nerve.

Moreover, second electrode portion 618 is biased to self-wrap at least partially about a circumference of the nerve, which in turn aligns second electrode portion 617 to be generally parallel to a longitudinal axis of the nerve and for contact with the nerve in that alignment. At the same time, the self-wrapping properties of second electrode portion 618 places the electrodes of array 630 in contact with the nerve.

In one embodiment, second electrode portion 618 has length (L4) sufficient to extend about at least one-third to one-half of a circumference of the nerve and in some embodiments, second electrode portion 618 has a length (L4) to extend substantially completely about an entire circumference of the nerve.

FIG. 20 is a diagram 650 that schematically illustrates a sectional view (a) and a side view of a nerve (b) when electrode cuff 610 is deployed on a nerve, according to an embodiment of the present disclosure. As shown in FIG. 20, electrodes 632, 634, 626, 636 generally encircle and contact the nerve 601 while electrodes 622, 626, 624 extend along the length of and contact the nerve 601. In this way, the electrode cuff 610 is positioned to apply a stimulation signal using the second electrode array 630 (electrodes 632, 634, 626, 636) or the first electrode array 620 (electrodes 622, 626, 624) or some combination of some of the electrodes of the two different arrays 620, 630. In this latter arrangement, during an implantation and testing phase, a controller is used to determine which combination of electrodes produces the most efficacious stimulation signal and going forward, that combination of electrodes is used to apply the therapeutic treatment. Of course, it will be understood that via the controller, additional adjustments regarding the selection of active electrodes can be made after implantation and after some period of treatment.

Although specific embodiments have been illustrated and described herein, it will be appreciated by those of ordinary skill in the art that a variety of alternate and/or equivalent implementations may be substituted for the specific embodiments shown and described without departing from the scope of the present disclosure. This application is intended to cover any adaptations or variations of the specific embodiments discussed herein.

What is claimed is:

1. An electrode cuff comprising:
a first elongate portion configured with a length to removably contact, and be aligned generally parallel to, length of a nerve, the first elongate portion having a first side edge and a second opposite side edge, both of which extend generally parallel to the length of the first elongate portion;
a second elongate portion to extend outwardly from, and perpendicular relative to, the first edge of the first elongate portion, wherein the second elongate portion is biased to, and has a length sufficient to, releasably encircle the nerve and at least partially overlap the second opposite side edge of the first elongate portion; and
a first single series of at least three electrodes disposed on and spaced apart longitudinally along the length of the first elongate portion,
wherein the at least partially overlapping portion of the second elongate portion has a width less than the length of the first elongate portion, with the width being less than a distance of separation between two outer electrodes of the at least three electrodes extending along the length of the first elongate portion.

2. The cuff of claim 1 comprising:
a second series of electrodes disposed on, and extending along a length of, the second elongate portion.

3. The cuff of claim 2, wherein the second single series of electrodes bifurcates the first single series of electrodes and a respective one of the second single series of electrodes defines a respective one of the first single series of electrodes.

4. The cuff of claim 2, wherein the second single series of electrodes is located at an end of the first single series of electrodes and a respective one of the second single series of electrodes defines a respective one of the first single series of electrodes.

5. The cuff of claim 1, wherein the first elongate portion defines a cuff body including a distal end, a proximal end, and a midportion, and wherein a base of the second elongate portion extends from the mid portion of the cuff body, and wherein the width of the second elongate portion is at least twice a width of the central electrode of the at least three electrodes.

6. The cuff of claim 1, wherein the second elongate portion comprises a single member and an only elongate portion extending from the respective opposite side edges of the first elongate portion.

7. The cuff of claim 1, wherein the first elongate portion defines a cuff body including a distal end, a proximal end, and a mid-portion, and wherein a base of the second elongate portion extends from the mid portion of the cuff body,
wherein the second elongate portion includes a distal portion, a proximal portion, and a waist portion interposed between the respective distal and proximal portions,
wherein a width of the waist portion is at least twice a width of the central electrode of the at least three electrodes, and
wherein the distal portion and the proximal portion each have a width substantially greater than the width of the waist portion and greater than a gap between adjacent nerve branches through which the waist portion extends with the respective distal and proximal portions of the second elongate portion positionable on opposite sides of the gap.

8. The cuff of claim 7, wherein the second elongate portion does not include any electrodes.

9. An electrode cuff comprising:
a first elongate portion configured with a length to removably contact, and be aligned generally parallel to, a length of a nerve, the first elongate portion having a first side edge and a second opposite side edge, both of which extend generally parallel to the length of the first elongate portion;
a second elongate portion to extend outwardly at an angle between 40 to 50 degrees relative to the first side edge of the first elongate portion, wherein the second elongate portion is biased to, and has a length sufficient to, releasably encircle the nerve and at least partially overlap the second opposite side edge of the first elongate portion; and
a first single series of at least three electrodes disposed on and spaced apart longitudinally along the length of the first elongate portion,
wherein the at least partially overlapping portion of the second elongate portion has a width less than the length of the first elongate portion, with the width being less than a distance of separation between two outer electrodes of the at least three electrodes that extend along the length the first elongate portion.

10. The cuff of claim 9, wherein the first elongate portion includes a distal end and a proximal end, wherein the second elongate portion comprises an only elongate portion extending from respective opposite side edges of the first elongate portion, wherein the second elongate portion includes a base and a tip, with the base of the second elongate portion extending only from the proximal end of the first elongate portion and the second elongate portion sized and shaped to cause the tip of the second elongate portion to releasably contact only the distal end of the first elongate portion.

11. The cuff of claim 10, wherein the first elongate portion includes a side edge defining a notched portion extending from the distal end of the first elongate portion proximally for a distance that is one-quarter to one-third of a length of the first elongate portion.

12. The cuff of claim 9, wherein the first elongate portion includes a distal end and a proximal end, and the second elongate portion includes a base and a tip, wherein the base of the second elongate portion is connected to, and extends only from, the distal end of the first elongate portion, and wherein the tip of the second elongate portion releasably contacts only the proximal end of the first elongate portion.

13. A method of implanting a nerve electrode cuff, comprising:
maneuvering an electrode cuff within a body to position a length of a first elongate portion of the electrode cuff to be aligned generally parallel to, and removably contact, a length of a first nerve, wherein the first elongate portion includes a first side edge and a second opposite side edge, both of which extend generally parallel to the length of the first elongate portion;
providing the electrode cuff to include a first single series of at least three electrodes disposed on and spaced apart longitudinally along the first elongate portion;
providing the electrode cuff to include a second elongate portion to extend outwardly at an angle relative to a first side edge of the first elongate portion;
maneuvering the second elongate portion to extend between adjacent nerve branches extending outward from the first nerve, wherein the second elongate portion is biased to, and has a length sufficient to, encircle the first nerve with a distal end of the second elongate portion at least partially overlapping with a second opposite side edge of the first elongate portion, wherein a width of the at least partially overlapping portion of the second elongate portion is less than the length of the first elongate portion and less than a distance of separation between two outer electrodes of the at least three electrodes extending along the length of the first elongate portion, and wherein the width of the second elongate portion is less than a gap between the two adjacent nerve branches.

14. The method of claim 13, wherein the angle is 40 to 50 degrees, and wherein the method comprises:
arranging a proximal end of the second elongate portion to be connected to, and extend from, only a proximal end of the first elongate portion and arranging the opposite distal end of the second elongate portion to be in releasable contact with only an opposite distal end of the first elongate portion.

15. The method of claim 13, wherein the angle is 90 degrees, and comprising:
arranging a first end of the second elongate portion to be connected to, and extend from, only midportion of the first elongate portion.

16. The method of claim 15, comprising:
arranging the second elongate portion to include a second single series of at least three electrodes extending along a length of the second elongate portion.

* * * * *